(12) United States Patent
Yoon et al.

(10) Patent No.: US 7,563,897 B2
(45) Date of Patent: Jul. 21, 2009

(54) NAPHTHALENE DIIMIDE-ZN(II) COMPLEX HAVING SELECTIVITY FOR PYROPHOSPHATE, PREPARATION METHOD THEREOF AND DETECTING METHOD OF PYROPHOSPHATE USING THE SAME

(75) Inventors: Ju Young Yoon, Seoul (KR); Ha Na Lee, Seoul (KR); Sook Kyung Kim, Seoul (KR)

(73) Assignee: EWHA University-Industry Collaboration Foundation, Seoul (KR)

( * ) Notice: Subject to any disclaimer, the term of this patent is extended or adjusted under 35 U.S.C. 154(b) by 0 days.

(21) Appl. No.: 11/968,120

(22) Filed: Dec. 31, 2007

(65) Prior Publication Data

US 2008/0261196 A1    Oct. 23, 2008

(51) Int. Cl.
*C07F 15/00* (2006.01)
*C12Q 1/68* (2006.01)
*G01N 33/53* (2006.01)

(52) U.S. Cl. .................. 546/2; 546/10; 435/6; 435/7.1; 435/7.2

(58) Field of Classification Search ...................... 435/6, 435/7.1, 7.2; 546/2, 10
See application file for complete search history.

(56) References Cited

OTHER PUBLICATIONS

Ramón Martínez-Máñez and Félix Sancenón, Chem. Rev. 2003, 103, 4419.
Mostafa Ronaghi, Samer Karamohamed, Bertil Pettersson, Mathias Uhlén, and Pål Nyrén, Anal. Biochem. 1996, 242, 84.
Shunqing Xu, Min He, Hongping Yu, Xiaokun Cai, Xianglin Tan, Bin Lu, and Baihua Shu, Anal. Biochem. 2001, 299, 188.
N. Jiten Singh, Eun Jin Jun, Kavitha Cheliappan, Daniel Thangadurai, R. Prakash Chandran, In-Chul Hwang, Juyoung Yoon, and Kwang S. Kim, Org. Lett. 2007, 9, 485.
Sook Kyung Kim, N. Jiten Singh, Jiyoung Kwon, In-Chul Hwang, Su Jin Park, Kwang S. Kim and Juyoung Yoon, Tetrahedron 2006, 62, 6065.
Thorfinnur Gunnlaugsson, Anthony P. Davis, John E. O'Brien and Mark Glynn, Org. Biomol. Chem. 2005, 3, 48.
Dmitry Aldakov and Pavel Anzenbacher, Jr, Chem. Commun. 2003, 1394.
Thorfinnur Gunnlaugsson, Anthony P. Davis, John E. O'Brien, and Mark Glynn, Org. Lett. 2002, 4, 2449.
Pavel Anzenbacher, Jr., Karolina Jursíková, and Jonathan L. Sessler, J. Am. Chem. Soc. 2000, 122, 9350.
Seiichi Nishizawa, Yuichi Kato, and Norio Teramae, J. Am. Chem. Soc. 1999, 121, 9463.
Han Na Lee, K. M. K. Swamy, Sook Kyung Kim, Ji-Young Kwon, Youngmee Kim,Sung-Jin Kim, Yeo Joon Yoon, and Juyoung Yoon, Org. Lett. 2007, 9, 243.
Yun Jung Jang, Eun Jin Jun, Yoon Ju Lee, Youn Sang Kim, Jong Seung Kim, and Juyoung Yoon, J. Org. Chem. 2005, 70, 9603.

(Continued)

*Primary Examiner*—Jezia Riley
(74) *Attorney, Agent, or Firm*—Lucas & Mercanti, LLP

(57) ABSTRACT

The present invention provides a novel fluorescent chemosensor including a naphthalene diimide-Zn(II) complex, which can efficiently recognize pyrophosphate (PPi) at pH 7.4. The fluorescent chemosensor exhibits a new kind of excimer fluorescence, which is selective for PPi in 100% aqueous solution. Further, since the naphthalene diimide-Zn(II) complex of the present invention does not couple with inorganic phosphate (Pi) or adenosine triphosphate (ATP) and has high selectivity for PPi, it can be usefully used to detect pyrophosphate (PPi), which serves to transfer signals and store energy in living organisms.

8 Claims, 6 Drawing Sheets

OTHER PUBLICATIONS

Hong Kwan Cho, Dong Hoon Lee and Jong-In Hong, Chem Commun. 2005, 1690.

Dong Hoon Lee, Soon Young Kim, and Jong-In Hong, Angew. Chem., Int. Ed. 2004, 43, 4777.

Dmitry Aldakov and Pavel Anzenbacher, Jr., J. Am. Chem. Soc. 2004, 126, 4752.

Shin Mizukami, Tetsuo Nagano, Yasuteru Urano, Akira Odani, and Kazuya Kikuchi, J. Am. Chem. Soc. 2002, 124, 3920.

David H. Vance and Anthony W. Czarnik, J. Am. Chem. Soc. 1994, 116, 9397.

Luigi Fabbrizzi, Nathalie Marcotte, Floriana Stomeo, and Angelo Taglietti, Angew. Chem., Int. Ed. Engl. 2002, 41, 3811.

Christopher Incarvito, Matthew Lam, Brian Rhatigan, Arnold L. Rheingold, C. Jin Qin, Anna L. Gavrilova and B. Bosnich, J. Chem. Soc., Dalton Trans., 2001, 3478.

Ji Young Kwon, Yun Jung Jang, Yoon Ju Lee, Kwan Mook Kim, Mi Sook Seo, Wonwoo Nam, and Juyoung Yoon, J. Am. Chem. Soc. 2005, 127(28), 10107.

Ha Na Lee et al. "Pyrophosphate-Selective Fluorescent Chemosensor at Physiological pH: Formation of a Unique Excimer upon Addition of Pyrophhosphate" JACS Communications Mar. 10, 2007.

NAPHTHALENE DIIMIDE-ZN(II) COMPLEX HAVING SELECTIVITY FOR PYROPHOSPHATE, PREPARATION METHOD THEREOF AND DETECTING METHOD OF PYROPHOSPHATE USING THE SAME

BACKGROUND OF THE INVENTION

1. Field of the Invention

The present invention relates to a naphthalene diimide derivative, and, more particularly, to a naphthalene diimide-Zn(II) complex having selectivity for pyrophosphate, a method of preparing the complex and a method of detecting pyrophosphate using the complex.

2. Description of the Related Art

Recently, novel sensors for detecting essential substances and ions present in living organisms have been actively designed and researched. Supramolecular chemistry has greatly influenced the design of host compounds, which can be selectively coupled with ions or various kinds of guest compounds. Thus, fluorescent chemosensors, which make it easy to observe the selective coupling of the host compounds and the guest compounds using the change in fluorescence of fluorescent materials coupled with supramolecular compounds, have been developed.

The term "fluorescence" refers to a photochemical phenomenon occurring when photons having a predetermined wavelength (excitation wavelength) collide with indicator molecules, by which electrons are excited to a high energy level. Among various analysis methods, fluorescence analysis is very advantageous in that signals can be observed even at a concentration as low as $10^{-9}$ M due to the high sensitivity thereof.

Recently, research on fluorescent chemosensors for detecting cations, anions and neutral organic molecules using the photochemical phenomenon has been actively conducted.

Anions play an important role in wide-ranging chemical and biological processes. Therefore, fluorescent chemosensors based on anion-induced changes are considered very interesting because they have high upper detection limits and are easy to handle (Martinez-Manez R and Sancanon F, *Chem. Rev.* 2003, 103, 4419). In particular, phosphate ions and derivatives thereof play an important role in the transfer of signals and the storage of energy in the biological system. For example, pyrophosphate (PPi) is a product obtained by hydrolyzing ATP under cellular conditions, and is a biologically important target. The detection of pyrophosphate (PPi) has been conducted using a real-time DNA sequencing method (Ronaghi M et al., *Anal. Biochem.* 1996, 242, 84). Currently, the detection of pyrophosphate is also used for cancer research (Xu S et al., *Anal. Biochem.* 2001, 299, 188).

The detection and discrimination of pyrophosphate (PPi) based on changes in fluorescence has been a major goal of many research groups (Singh N J et al., *Org. Lett.* 2007, 9, 485; Kim S K et al., *Tetrahedron* 2006, 62, 6065; Gunnlaugsson T et al., *Org. Biomol. Chem.* 2005, 3, 48; Aldakov D and Anzenbacher P Jr., *Chem. Comm.* 2003, 1394; Gunnlaugsson T et al., *Org. Lett.* 2002, 4, 2449; Anzenbacher P et al., *J. Am. Chem. Soc.* 2000, 122, 9350 Nishizawa S et al., *J. Am. Chem. Soc.* 1999, 121, 9463; Lee H N et al., *Org. Lett.* 2007, 9, 243; Jang Y J et al., *J. Org. Chem.* 2005, 70, 9603; Cho H K et al., *Chem Commun.* 2005, 1690; Lee D H et al., *Angew. Chem., Int. Ed.* 2004, 43, 4777; Aldakov D and Anzenbacher P Jr., *J. Am. Chem. Soc.* 2004, 126, 4752; Mizukami S et al. *J. Am. Chem. Soc.* 2002, 124, 3920; Vance D H and Czarnik A W, *J. Am. Chem. Soc.* 1994, 116, 9397). In relation to this, the present inventors have reported that novel fluorescein derivatives exhibit prominent fluorescence amplification of red-shift when pyrophosphate (PPi) is added thereto at pH 7.4.

As described above, although various kinds of fluorescent chemosensors, which can selectively recognize pyrophosphate (PPi), have been disclosed, few fluorescent chemosensors that can recognize pyrophosphate (PPi) in aqueous solutions that are similar to the environment in living organisms have been disclosed (Jang Y J et al., *J. Org. Chem.* 2005, 70, 9603; Lee D H et al., *Angew. Chem., Int. Ed. Engl.* 2004, 43, 4777; Fabbrizzi L et al., *Angew. Chem., Int. Ed. Engl.* 2002, 41, 3811; Mizukami S et al., *J. Am. Chem. Soc.* 2002, 124, 3920), and only two kinds of fluorescent chemosensors based on the formation of excimers have been disclosed.

The term "excimer fluorescence" refers to a phenomenon in which, as the distance between fluorescent materials is decreased, energy is transferred therebetween, and thus a new kind of fluorescence is emitted at a longer wavelength than that of the maximum fluorescence value emitted from the original fluorescent material. Excimer fluorescence is advantageous in that, since fluorescence can be observed at a new maximum fluorescence value, fluorescence correction is not required, and thus changes in fluorescence are more positively discerned.

Teramae et al. have detected pyrophosphate (PPi) using a guanidium-pyrene system, but this guanidium-pyrene system was tested only in methanol, and, in this system, the selectivity for pyrophosphate (PPi) was only compared to that for inorganic phosphate (Pi) (Nishizawa S et al., *J. Am. Chem. Soc.* 1999, 121, 9463). Further, Hong et al. have reported a pyrene-Zn(II) complex as a PPi-selective fluorescent chemosensor, but this pyrene-Zn(II) complex was problematic in that it causes the formation of excimers corresponding to the reaction of ATP with PPi even if only a small amount (0.4 equivalents) of ATP is used (Lee D H et al., *Angew. Chem., Int. Ed.* 2004, 43, 4777).

As described above, to date, no fluorescent chemosensors having excellent selectivity for PPi compared to selectivity for ATP and Pi due to the formation of excimers in an aqueous solution have been reported.

SUMMARY OF THE INVENTION

Therefore, the present inventors, researching fluorescent chemosensors having selectivity for pyrophosphate, have synthesized a naphthalene diimide-Zn(II) complex, and found that the naphthalene diimide-Zn(II) complex emits excimer fluorescence that is selective for pyrophosphate (PPi) at a wavelength of 490 nm. Based on this finding, the present invention was completed.

Accordingly, the present invention provides a naphthalene diimide-Zn(II) complex having selectivity for pyrophosphate.

Further, the present invention provides an intermediate of the naphthalene diimide-Zn(II) complex having selectivity for pyrophosphate.

Further, the present invention provides a method of preparing the naphthalene diimide-Zn(II) complex.

Further, the present invention provides a method of detecting pyrophosphate using the naphthalene diimide-Zn(II) complex.

The present invention provides a naphthalene diimide-Zn(II) complex having selectivity for pyrophosphate, represented by Formula 1 below.

[Formula 2]

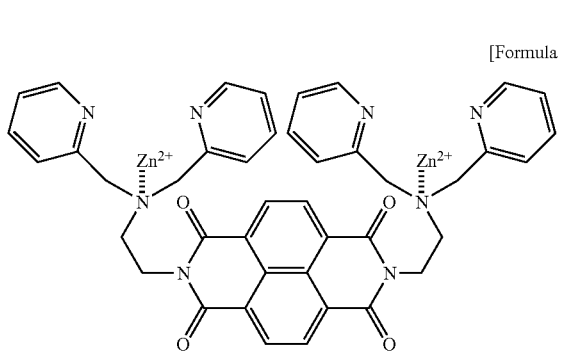

Further, the present invention provides an intermediate compound of naphthalene diimide-Zn(II) complex having selectivity for pyrophosphate, represented by Formula 2 below.

[Formula 2]

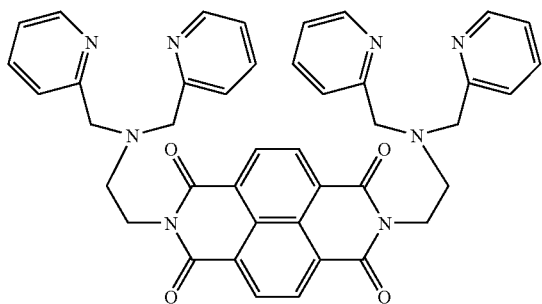

Further, the present invention provides a method of preparing the naphthalene diimide-Zn(II) complex having selectivity for pyrophosphate.

The method of preparing the naphthalene diimide-Zn(II) complex according to the present invention includes reacting the compound, represented by Formula 2 above, with zinc nitrate. This compound, represented by Formula 2 above, is prepared by adding (2-amino ethyl)bis(2-pyridyl methyl) amine to naphthalene-1,4,5,8-tetracarboxylic dianhydride.

Specifically, the method of preparing the naphthalene diimide-Zn(II) complex according to the present invention is represented by Reaction Formula 1 below.

[Reaction Formula 1]

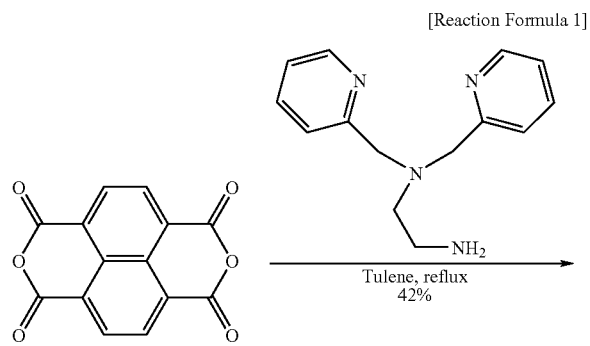

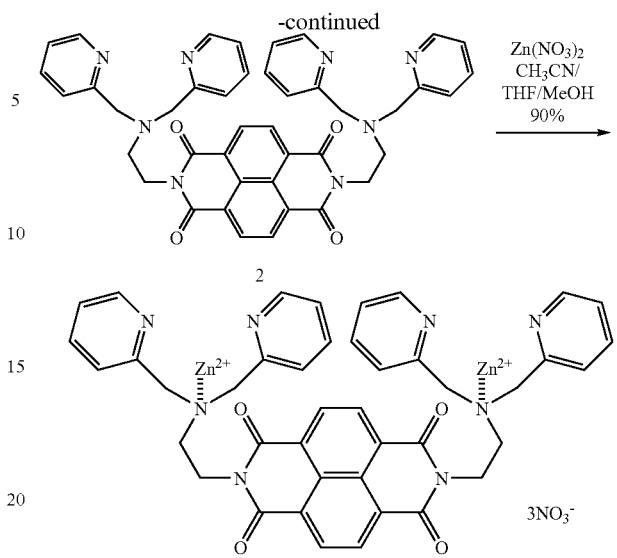

Further, the present invention provides a method of detecting pyrophosphate using the naphthalene diimide-Zn(II) complex represented by Formula 1 above.

In the compound, represented by Formula 1 above, according to the present invention, when other anions, such as ATP, ADP, AMP, Pi, $HSO_4^-$, $CH_3CO_2^-$, $I^-$, $Br^-$, $Cl^-$, and $F^-$, are added to the compound at pH 7.4, a certain significant change in fluorescence does not occur. However, when pyrophosphate (PPi) is added thereto, a considerable fluorescence increase, attributable to the formation of excimers at a wavelength of 490 nm, is observed. Therefore, the compound, represented by Formula 1 above, according to the present invention, can be used as a fluorescent chemosensor having selectivity for pyrophosphate (PPi).

In particular, the fluorescent chemosensor of the present invention is selectively coupled with PPi even when ATP, Pi and PPi coexist, so that new excimer peaks are formed, with the result that the fluorescent chemosensor can selectively detect only PPi. Accordingly, the fluorescent chemosensor of the present invention can be used as a fluorescent chemosensor having selectivity for PPi.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
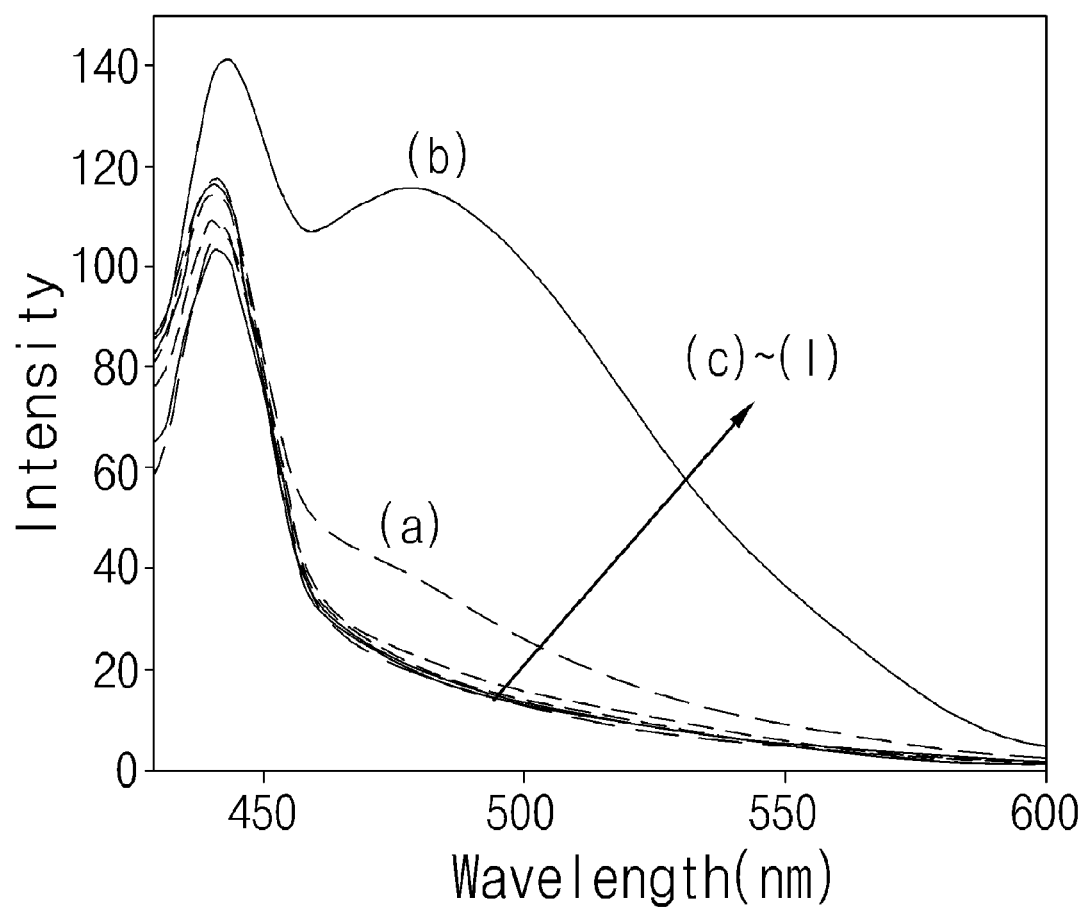
FIG. 1 is a graph showing fluorescence change curves when 100 equivalents of Pi(i), PPi(b) and several anions, such as ATP (adenosine triphosphate(a)), ADP (adenosine diphosphate(k)), AMP (adenosine monophosphate(l)), $CH_3CO_2^-$ (h), $HSO_4^-$(j), $F^-$(d), $Cl^-$(g), $Br^-$(e) and $I^-$(f), are added to the compound (6 μM), represented by Formula 1(c), at pH 7.4 (10 mM HEPES buffer solution)

Hereinafter, the present invention will be described in detail with reference to Examples.

A better understanding of the present invention may be obtained through the following examples, which are set forth to illustrate, but are not to be construed as the limit of, the present invention.

EXAMPLE 1

Preparation of Compound Represented by Formula 2[Intermediate Compound of Naphthalene Diimide-Zn(II) Complex]

(2-Amino ethyl)bis(2-pyridyl methyl)amine (200 mg, 0.83 mmol)(Incarvito C et al., *J. Chem. Soc., Dalton Trans.*, 2001, 3478) was dropped into naphthalene-1,4,5,8-tetracarboxylic dianhydride (74 mg, 0.275 mmol) (N818, Aldrich, USA), which was dissolved in 50 mL toluene, for 5 minutes. The resulting mixture was refluxed at a temperature of 135° C. for 5 hours, and then toluene was evaporated from the mixture in a vacuum. Subsequently, the remaining solid was recrystallized with ethanol and then refined, thus obtaining a yellow powdered compound (249 mg, yield 42%) represented by Formula 2.

mp>300° C.;

$^1$H NMR (CDCl$_3$, 250 MHz) δ 8.63 (s, 4H), 8.30 (d, 4H, J=4.6 Hz), 7.27 (m, 8H), 6.94 (m, 4H), 4.36 (t, 4H, J=6 Hz), 3.86 (s, 8H), 2.91 (t, 4H, J=6 Hz);

$^{13}$C NMR (CDCl$_3$, 62.5 MHz) δ 162.8, 159.6, 149.1, 136.3, 131.0, 126.8, 123.1, 122.0, 60.5, 51.5, 38.7;

HRMS (FAB) m/z=717.2941 (M+H)$^+$, calc. for C$_{42}$H$_{37}$N$_8$O$_4$=717.2938.

EXAMPLE 2

Preparation of Compound Represented by Formula 1[Naphthalene Diimide-Zn(II) Complex]

2 ml of a 170 mM zinc nitrate methanol solution was dropped into the compound (100 mg, 0.14 mmol), represented by Formula 2, obtained in Example 1, which was dissolved in CH$_3$Cl—CH$_3$CN (10:1, 5.5 ml). The resulting mixture was stirred at room temperature for 30 minutes. Subsequently, the resulting precipitate was filtered, and was then washed using chloroform, cold acetonitrile and methanol, thus obtaining a yellow powdered compound (129 mg, yield 90%) represented by Formula 1.

mp>300° C., decompose.;

$^1$H NMR (D$_2$O, 250 MHz) δ 8.55 (d, 4H, J=5 Hz), 8.27 (s, 4H), 8.00 (t, 4H, J=6.5 Hz), 7.59 (d, 4H, J=7.9 Hz), 7.54 (t, 4H, J=5.9 Hz), 4.55 (d, 4H, J=16.2 Hz), 4.30 (brt, 4H), 4.18 (d, 4H, J=16.2 Hz), 3.83 (brt, 4H);

$^{13}$C NMR (D$_2$O, 62.5 MHz) δ 163.6, 154.2, 147.6, 141.2, 130.7, 125.8, 124.9, 124.7, 62.4, 56.4, 49.1;

ESI MS (FAB) m/z=1030.1 (M)$^+$, calc. for C$_{42}$H$_{36}$N$_{11}$O$_{13}$Zn$_2$=1030.1.

EXPERIMENTAL EXAMPLE 1

Observation of Fluorescence Change 1-1: Experiment to Determine Fluorescence Attributable to the Coupling of the Compound Represented by Formula 1 with Pyrophosphate or Other Anions In order to examine the coupling characteristics between the compound, represented by Formula 1, and pyrophosphate (PPi) or other anions (ATP, ADP, AMP, Pi, HSO$_4^-$, CH$_3$CO$_2^-$, I$^-$, Br$^-$, Cl$^-$ and F$^-$), the following experiment was conducted.

A solution (10 mM) for storing sodium salts of PPi, Pi, ATP, ADP and AMP, and a solution (1 mM) for storing anions of tetrabutyl ammonium salt, such as HSO$_4^-$, CH$_3$CO$_2^-$, I$^-$, Br$^-$, Cl$^-$ and F$^-$, were prepared using respective 10 mM HEPES buffer solutions (pH 7.4). Further, a solution (1 mM) for storing the compound represented by Formula 1 obtained in Example 2 was prepared using doubly-distilled desalted water. These storage solutions were used on the day of preparation.

A test solution was used after 24 µl of a probe storage solution (the solution for storing the compound, represented by Formula 1, of the present invention) was put in a test tube such that the final concentration of the probe storage solution was 6 µM, 24 µl of each of the solutions for storing PPi and anions (ATP, ADP, AMP, Pi, HSO$_4^-$, CH$_3$CO$_2^-$, I$^-$, Br$^-$, Cl$^-$ and F$^-$) was added to the test tube such that the aliquot of each of the solutions was 10 equivalents, and then the mixed solution was diluted with 4 ml of a 10 mM HEPES buffer solution (pH 7.4). The total fluorescence change was measured using a spectrofluorophotometer (RF-5301/PC, Shimadzu), under the conditions that the excitation wavelength was 383 nm and the width of each of the excitation and emission slits was 10 nm, and the results thereof are shown in FIG. 1.

As shown in FIG. 1, in the emission spectrum of the compound, represented by Formula 1, according to the present invention, when PPi was added at pH 7.4, an excimer peak was observed at a wavelength of 490 nm. In contrast, when 10 equivalents of other anions were added, no change was observed. Therefore, it can be seen that the compound represented by Formula 1 according to the present invention is selectively coupled with PPi.

1-2. Fluorescence Titration Experiment on the Compound Represented by Formula 1 Depending on the Concentration of Pyrophosphate In order to examine the coupling characteristics between the compound represented by Formula 1 and pyrophosphate (PPi), the following experiment was conducted.

A solution (10 mM) for storing sodium pyrophosphate was prepared using a 10 mM HEPES buffer solution (pH 7.4). Further, a solution (1 mM) for storing the compound represented by Formula 1 obtained in Example 2 was prepared using doubly-distilled desalted water. These storage solutions were used on the day of preparation.

A test solution 1 was used after 24 µl of a probe storage solution (the solution for storing the compound represented by Formula 1 of the present invention) was put in a test tube such that the final concentration of the probe storage solution was 6 µM, 0.72~12 µl of the solution for storing PPi was added to the test tube such that the aliquot thereof was 0.3~5 equivalents, and then the mixed solution was diluted with 4 ml of a 10 mM HEPES buffer solution (pH 7.4). The total fluorescence change was measured using a spectrofluorophotometer (RF-5301/PC, Shimadzu) under the conditions that the excitation wavelength was 383 nm and the width of each of the excitation and emission slits was 10 nm, and the results thereof are shown in FIG. 2.

Figure 2:
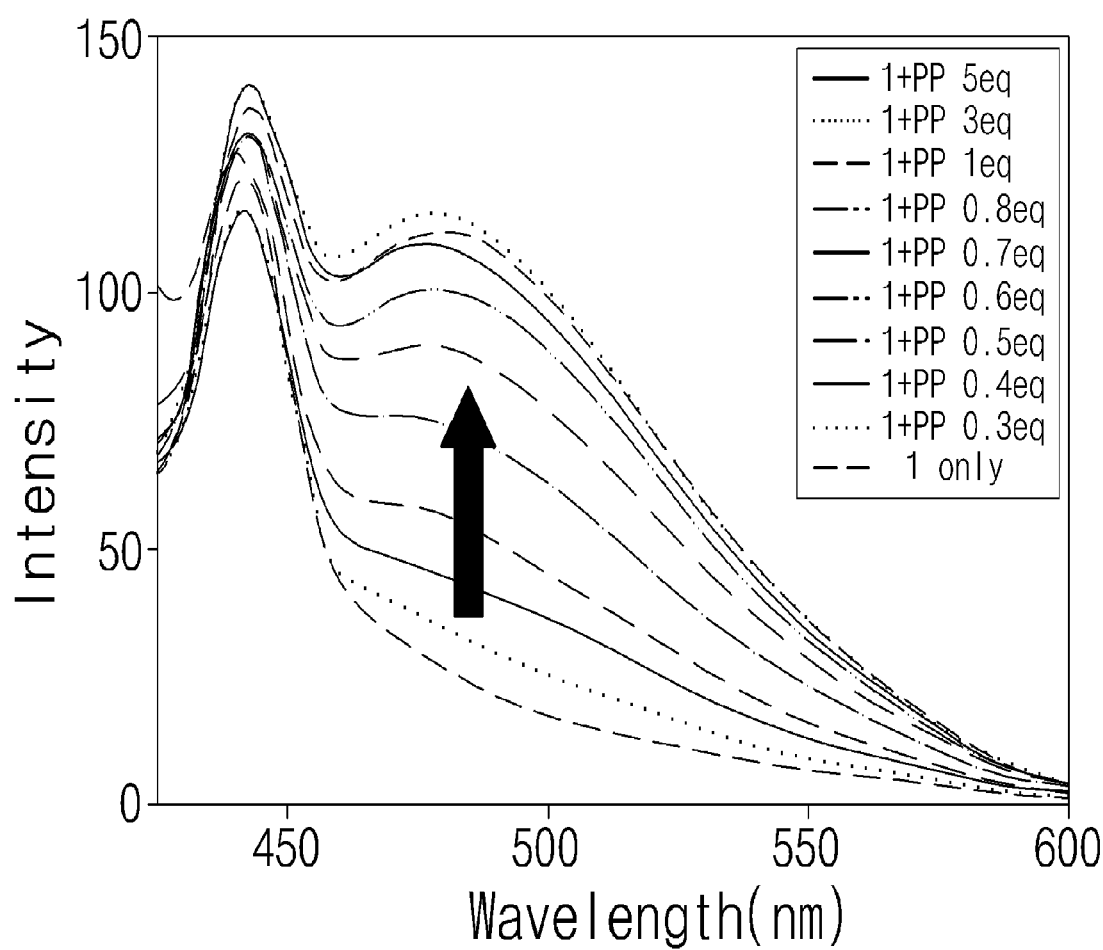
FIG. 2 is a graph showing fluorescence titration curves when PPi is added to the compound (6 μM) represented by Formula 1 at pH 7.4 (10 mM HEPES buffer solution) depending on the concentration (0.3~5 equivalents) of PPi.

As shown in FIG. 2, in the emission spectrum of the compound represented by Formula 1 according to the present invention, when the final concentration of the compound was 6 µM at pH 7.4, the amount of added PPi was increased from 0.3 equivalents to 5 equivalents, and thus a new fluorescence increase due to the formation of the excimer was observed at a wavelength of 490 nm. Therefore, it can be seen that the coupling constant of a complex of the compound of the present invention and PPi was $4.1 \times 10^5 M^{-1}$, through the fluorescence titration experiment of the compound and PPi.

1-3. Fluorescence Titration Experiment on the Compound Represented by Formula 1 when Inorganic Phosphate and Pyrophosphate Coexist In order to examine the coupling characteristics between the compound represented by Formula 1 and pyrophosphate (PPi) when inorganic phosphate and pyrophosphate coexist, the following experiment was conducted.

A solution (10 mM) for storing inorganic sodium phosphate and a solution (10 mM) for storing sodium pyrophosphate were prepared using a 10 mM HEPES buffer solution (pH 7.4). Further, a solution (1 mM) for storing the compound represented by Formula 1, obtained in Example 2, was prepared using doubly-distilled desalted water. These storage solutions were used on the day of preparation.

A test solution 1 was used after 24 µl of a probe storage solution (the solution for storing the compound, represented by Formula 1, of the present invention) was put in a test tube such that the final concentration of the probe storage solution was 6 µM, 240 µl of a solution for storing Pi was added to the test tube such that the aliquot thereof was 100 equivalents, 0.72~12 µl of the solution for storing PPi was added to the test tube such that the aliquot thereof was 0.3~5 equivalents, and then the mixed solution was diluted with 4 ml of a 10 mM HEPES buffer solution (pH 7.4). The total fluorescence change was measured using a spectrofluorophotometer (RF-5301/PC, Shimadzu) under the conditions that the excitation wavelength was 383 nm and the width of each of the excitation and emission slits was 10 nm, and the results thereof are shown in FIG. 3.

Figure 3:
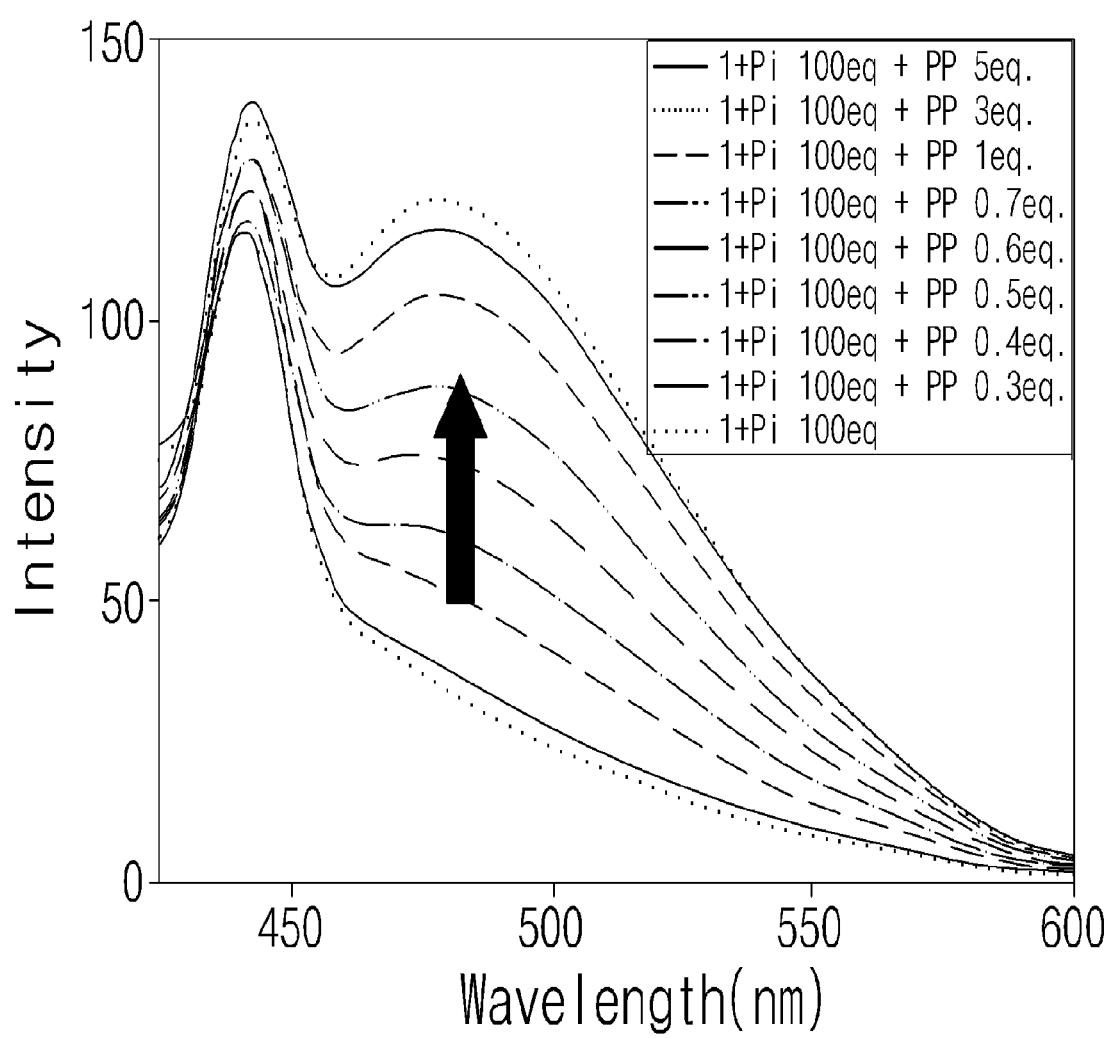
FIG. 3 is a graph showing fluorescence titration curves when PPi is added to the compound (6 μM) represented by Formula 1 at pH 7.4 (10 mM HEPES buffer solution) in the presence of 100 equivalents of Pi depending on the concentration (0.3~5 equivalents) of PPi.

As shown in FIG. 3, in the emission spectrum of the compound, represented by Formula 1, according to the present invention, even when the compound coexists with 100 equivalents of Pi at pH 7.4, the amount of added PPi was increased from 0.3 equivalents to 5 equivalents, and thus the formation of excimer fluorescence continuously increased at a wavelength of 490 nm. Therefore, it can be seen that the compound represented by Formula 1 according to the present invention can serve as a sensor having selectivity for PPi.

1-4. Fluorescence Titration Experiment on the Compound Represented by Formula 1 when ATP and Pyrophosphate Coexist In order to examine the coupling characteristics between the compound represented by Formula 1 and pyrophosphate (PPi) when ATP and pyrophosphate coexist, the following experiment was conducted.

A solution (10 mM) for storing sodium salt of ATP and a solution (10 mM) for storing sodium pyrophosphate were prepared using a 10 mM HEPES buffer solution (pH 7.4). Further, a solution (1 mM) for storing the compound represented by Formula 1, obtained in Example 2, was prepared using doubly-distilled desalted water. These storage solutions were used on the day of preparation.

A test solution 1 was used after 24 µl of a probe storage solution (the solution for storing the compound represented by Formula 1 of the present invention) was put in a test tube such that the final concentration of the probe storage solution was 6 µM, 24 µl of a solution for storing ATP was added to the test tube such that the aliquot thereof was 10 equivalents, 2.16~12 µl of the solution for storing PPi was added to the test tube such that the aliquot thereof was 0.5~5 equivalents, and then the mixed solution was diluted with 4 ml of a 10 mM HEPES buffer solution (pH 7.4). The total fluorescence change was measured using a spectrofluorophotometer (RF-5301/PC, Shimadzu) under the conditions that the excitation wavelength was 383 nm and the width of each of the excitation and emission slits was 10 nm, and the results thereof are shown in FIG. 4.

Figure 4:
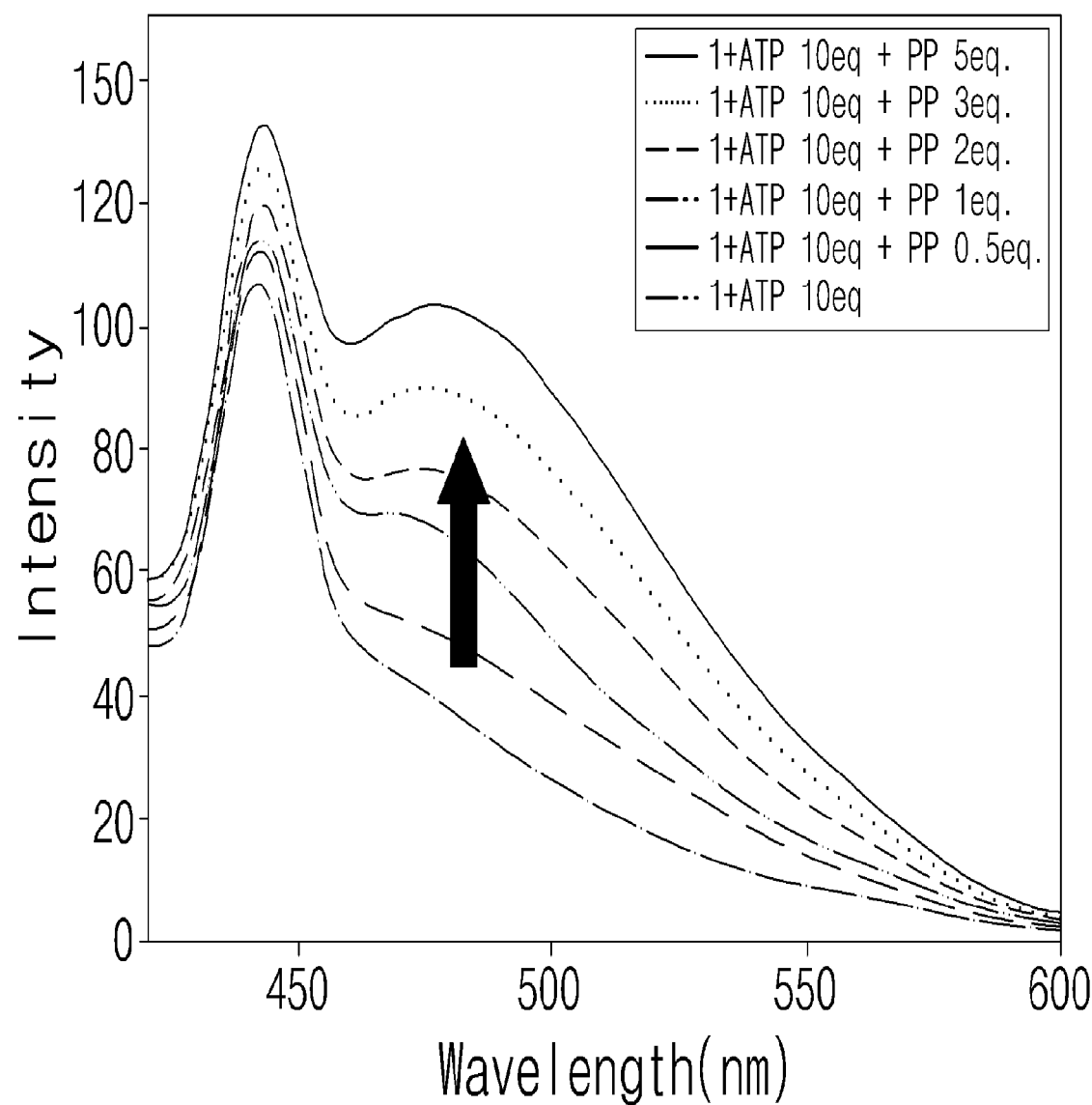
FIG. 4 is a graph showing fluorescence titration curves when PPi is added to the compound (6 µM) represented by Formula 1 at pH 7.4 (10 mM HEPES buffer solution) in the presence of 10 equivalents of ATP depending on the concentration (0.5~5 equivalents) of PPi.

As shown in FIG. 4, in the emission spectrum of the compound represented by Formula 1 according to the present invention, even when the compound coexists with 10 equivalents of ATP at pH 7.4, the amount of added PPi was increased from 0.5 equivalents to 5 equivalents, and thus the formation of excimer fluorescence continuously increased at a wavelength of 490 nm. Therefore, it can be seen that the compound represented by Formula 1 according to the present invention can serve as a sensor having selectivity for PPi.

EXPERIMENTAL EXAMPLE 2

Mass Analysis of a Complex of the Compound Represented by FORMULA 1 and Pyrophosphate using Electrospray Ionization (ESI)

In order to evaluate whether or not a complex of the compound represented by Formula 1 according to the present invention and pyrophosphate was formed, electrospray ionization mass analysis was conducted with reference to the document (KWON JY et al., *J. Am. Chem. Soc.* 2005, 127 (28), 10107).

Figure 5:
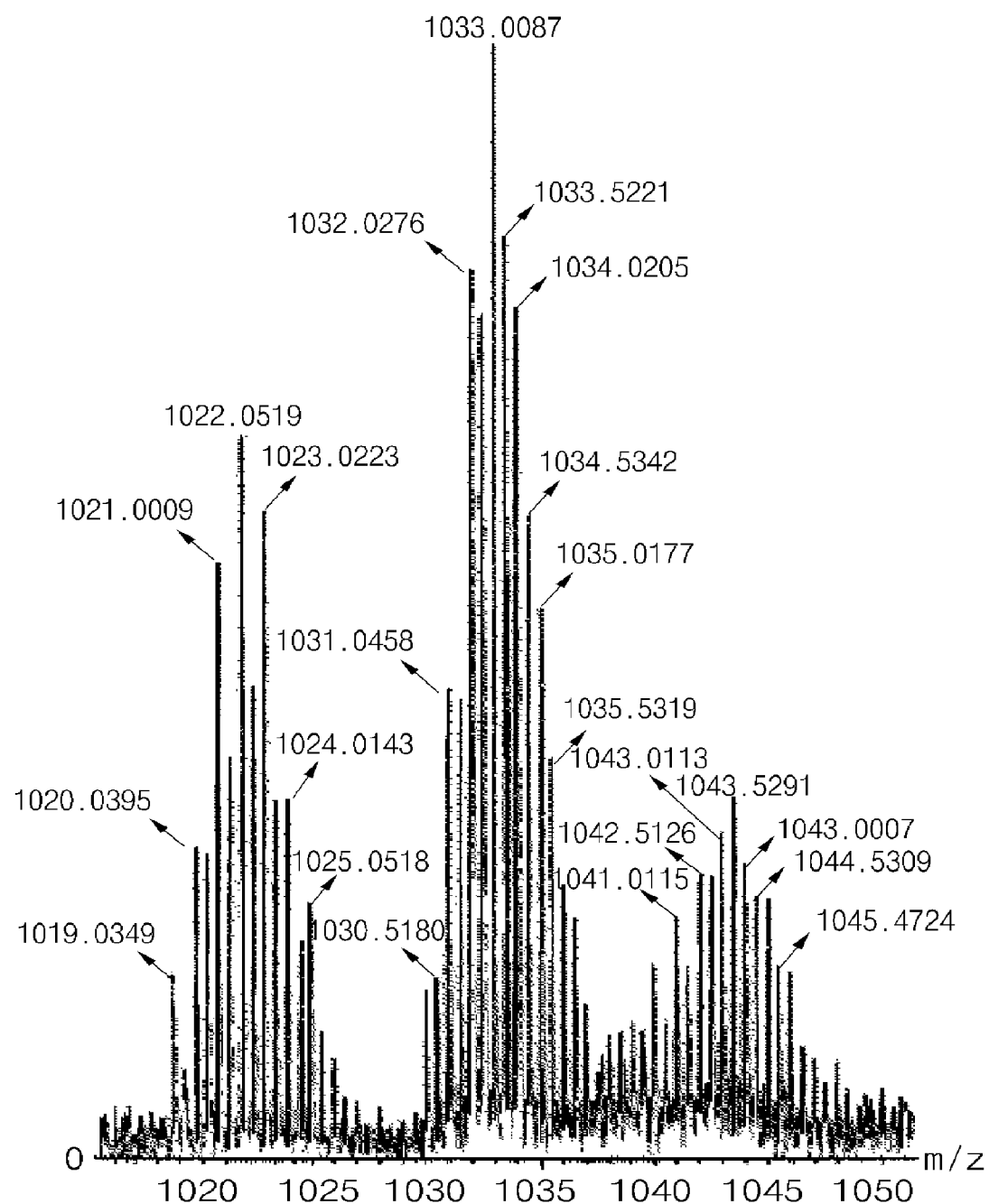
FIG. 5 is a graph showing the results of ESI (electrospray ionization) mass analysis when the compound represented by Formula 1 (15 µM) and excess PPi (10 equivalents) are present.
Figure 6:
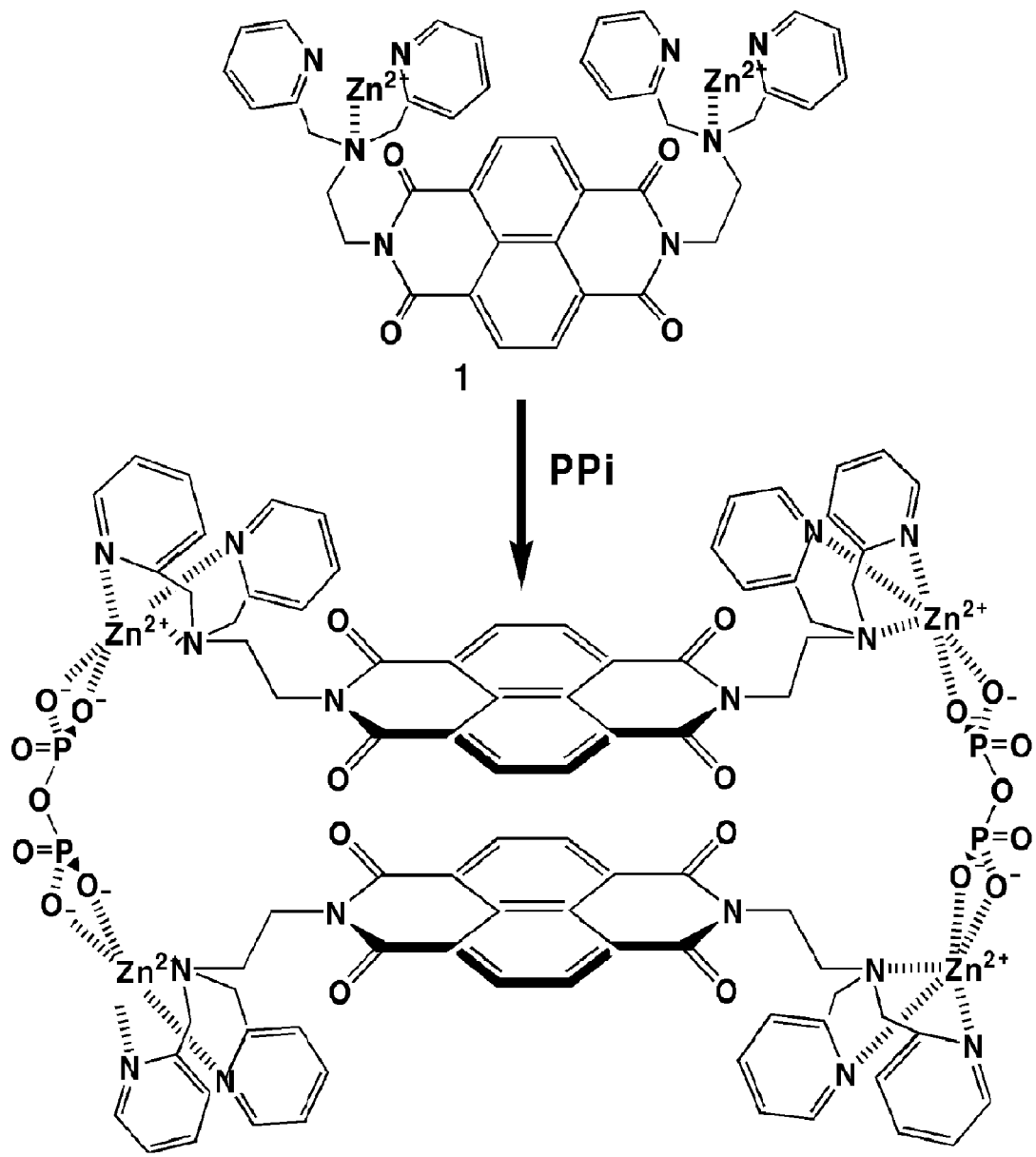
FIG. 6 is a view illustrating a mechanism for generating excimer fluorescence by coupling the compound represented by Formula 1 and PPi.

The compound (15 µM) represented by Formula 1 and 10 equivalents of sodium pyrophosphate (150 µM) were put into and dissolved in 5 ml of distilled desalted water to form a mixed solution, and then the mixed solution was mass-analyzed through electrospray ionization (ESI). As a result, three peaks were obtained in the range of m/z=1000-1050, as shown in FIG. 5 (instrument used: Thermo Finnigan LCQ™ Advantage MAX quadrupole ion trap instrument, San Jose, Calif., USA).

Since the three peaks, shown in FIG. 5, indicate masses corresponding to $[C_{84}H_{74}N_{16}O_{22}P_4Zn_4]^{2+}$ $(=[2\underline{1}+2\ PPi]^{2+})$, $[C_{84}H_{73}N_{16}NaO_{22}P_4Zn_4]^{2+}$ $(=[2\underline{1}+2PPi+Na^+-H^+]^{2+})$ and $[C_{84}H_{72}N_{16}Na_2O_{22}P_4Zn_4]^{2+}$ $(=[2\underline{1}+2PPi+2Na^+-2H^+]^{2+})$, respectively, it can be seen that each of them indicates a 2+2 structure in which two naphthalene diimide-Zn(II) molecules are coupled with two pyrophosphate molecules. Therefore, the formation of excimers is based on this result.

In the above, $\underline{1}$ is a compound represented by Formula 1 according to the present invention, that is, a naphthalene diimide-Zn(II) complex.

As the results of the excimer formation in Experimental Example 1 and the mass analysis in Experimental Example 2, it can be seen that the compound represented by Formula 1 according to the present invention was selectively coupled with PPi to form a 2+2 type excimer.

As described above, the naphthalene diimide-Zn(II) complex of the present invention does not recognize other anions in 100% aqueous solution, and has high selectivity for pyrophosphate (PPi). Specifically, in the naphthalene diimide-Zn (II) complex of the present invention, an excimer fluorescence peak attributable to the coupling of the complex and PPi is observed at a wavelength of 490 nm. Accordingly, the naphthalene diimide-Zn(II) complex of the present invention can be usefully used as a fluorescent chemosensor for selectively detecting pyrophosphate (PPi), which serves to transfer signals and store energy in living organisms.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A naphthalene diimide-Zn(II) complex having selectivity for pyrophosphate, represented by Formula 1 below

[Formula 1]

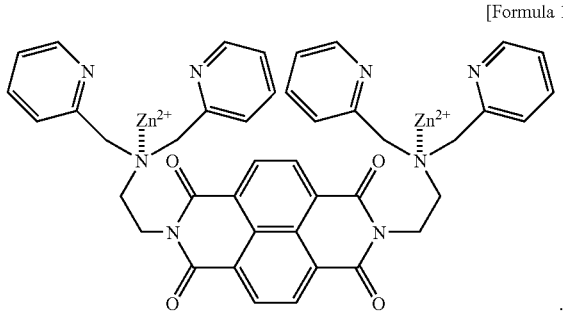

2. An intermediate compound of naphthalene diimide-Zn (II) complex having selectivity for pyrophosphate, represented by Formula 2 below

[Formula 2]

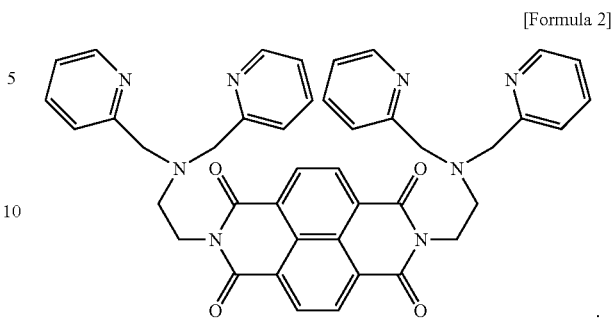

3. A method of preparing the naphthalene diimide-Zn(II) complex of claim 1, comprising: reacting a compound represented by Formula 2 below with zinc nitrate

[Formula 2]

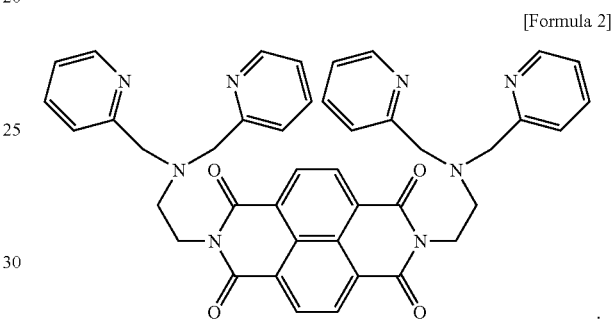

4. The method of preparing the naphthalene diimide-Zn(II) complex according to claim 3, wherein the compound represented by Formula 2 above is prepared by adding (2-amino ethyl)bis(2-pyridyl methyl)amine to naphthalene- 1,4,5,8-tetracarboxylic dianhydride.

5. A method of detecting pyrophosphate in a living organism comprising, treating a sample from the living organism with the naphthalene diimide-Zn(II) complex of claim 1 and detecting whether pyrophosphate is present in the sample.

6. The method of detecting pyrophosphate according to claim 5, wherein the pyrophosphate is detected by observing a fluorescence increase effect attributable to an excimer using an excitation wavelength of 383 nm and a measured wavelength of 490 nm.

7. A fluorescent sensor comprising the naphthalene diimide-Zn(II) complex of claim 1.

8. The fluorescent sensor according to claim 7, wherein the fluorescent sensor selectively detects pyrophosphate and couples with pyrophosphate.

\* \* \* \* \*